United States Patent
Jackson et al.

(10) Patent No.: US 7,655,187 B2
(45) Date of Patent: Feb. 2, 2010

(54) SYSTEMS FOR ISOLATING TOXINS AND COLLECTING ELUATES FOR TESTING FOR TOXINS AND METHODS USING THE SAME

(75) Inventors: Dennis E. Jackson, Nixa, MO (US); Nancy Zabe, Waltham, MA (US)

(73) Assignee: Waters Technologies Corporation, Milford, MA (US)

( * ) Notice: Subject to any disclaimer, the term of this patent is extended or adjusted under 35 U.S.C. 154(b) by 677 days.

(21) Appl. No.: 11/117,801

(22) Filed: Apr. 29, 2005

(65) Prior Publication Data
US 2006/0228255 A1   Oct. 12, 2006

Related U.S. Application Data

(60) Provisional application No. 60/661,971, filed on Mar. 11, 2005.

(51) Int. Cl.
*B01L 3/02* (2006.01)
*B01L 11/00* (2006.01)
*G01N 1/14* (2006.01)
*G01N 1/00* (2006.01)
*G01N 30/02* (2006.01)

(52) U.S. Cl. ............ 422/100; 422/70; 422/81; 422/101; 422/102; 422/103; 210/258; 210/635; 210/656; 436/161; 436/174; 435/6; 73/19.02; 73/23.35; 73/864.15; 73/864.16; 73/864.17; 73/864.18; 73/864.21

(58) Field of Classification Search ............... None
See application file for complete search history.

(56) References Cited

U.S. PATENT DOCUMENTS

| 4,104,026 A |   | 8/1978 | Brooker et al. |
| 4,106,911 A | * | 8/1978 | Marcelli ................ 422/63 |
| 4,655,915 A | * | 4/1987 | Carpinone ............ 210/167.26 |
| 4,709,577 A | * | 12/1987 | Thompson .............. 73/40.7 |
| 4,859,611 A | * | 8/1989 | Groopman et al. .......... 436/518 |
| 5,324,480 A |   | 6/1994 | Shumate et al. |
| 5,354,655 A | * | 10/1994 | Ward et al. .............. 435/6 |
| 5,413,562 A | * | 5/1995 | Swauger ............... 604/179 |
| 5,660,792 A |   | 8/1997 | Koike |
| 6,564,655 B1 |   | 5/2003 | Austen et al. |
| 2002/0054832 A1 |   | 5/2002 | Amirav et al. |
| 2004/0104173 A1 |   | 6/2004 | Manach et al. |
| 2004/0126890 A1 |   | 7/2004 | Gjerde et al. |
| 2005/0011821 A1 |   | 1/2005 | Held et al. |
| 2005/0011835 A1 |   | 1/2005 | Henderson et al. |

* cited by examiner

*Primary Examiner*—Jill Warden
*Assistant Examiner*—Neil Turk
(74) *Attorney, Agent, or Firm*—Edwards Angell Palmer & Dodge LLP; Peter C. Lauro, Esq.; George N. Chaclas

(57) ABSTRACT

The present invention provides systems for isolating toxins and collecting an eluate from a sampling column for subsequent testing and to methods of extracting and collecting an eluate using the same systems. Preferably, the systems comprise a sample holder such as an immuno-affinity column for holding the sample and a self-contained fluid delivery system that can deliver liquid, e.g., reagents, and gaseous fluids, e.g., compressed air. More preferably, the fluid control system of the fluid delivery system provides some amount of pressurized gas continuously to the headspace of the column even when a fluid is not being forced through the resin gel in the column.

26 Claims, 3 Drawing Sheets

SYSTEMS FOR ISOLATING TOXINS AND COLLECTING ELUATES FOR TESTING FOR TOXINS AND METHODS USING THE SAME

CROSS-REFERENCE TO RELATED APPLICATIONS

This application claims the benefit of priority from U.S. provisional application No. 60/661,971, which was filed on Mar. 11, 2005.

BACKGROUND OF THE INVENTION

1. Field of the Invention

The present invention relates to systems for isolating toxins and collecting an eluate for subsequent testing and to methods of isolating toxins and collecting an eluate using the same systems. More particularly, the present invention relates to systems for isolating toxins and collecting an eluate from a column for subsequent testing and to methods of isolating toxins and collecting an eluate using the same systems, wherein some amount of pressurized gas is continuously being delivered to the headspace of the column even when a fluid is not being forced through the resin gel in the column.

2. Background Art

The presence of microbial pathogens is a well-recognized cause of various medical and etiological problems. For example, microscopic fungi can produce toxins e.g., mycotoxins, that can be ingested, causing severe health complications and discomfort. These toxins can cause, among others, blood disease, cancer, nervous system disorders, kidney damage, and liver damage. Many of these fungi, can grow on plants, especially plants that produce grains for human and animal consumption. Thus, food contaminated with mycotoxins presents a serious health risk for humans as well.

e.g., grain, milk, food products, early on and quickly and with a high degree of certainty and at a high throughput.

Advanced bio-analytical toxicology screening is an essential part of quality food processing. This is especially true with respect to testing for aflatoxins, the predominant carcinogenic toxin found in the food supply. Vicam, Incorporated of Watertown, Mass. provides the food quality industry with methods and means for analyzing aflatoxins using an immuno-affinity column, i.e., the Afla-Test® column. U.S. Pat. Nos. 4,859,611 and 4,818,687 that disclose the Afla-Test® column are incorporated herein by reference.

The immuno-affinity column is substantially cylindrical in shape and open at both ends. A resin gel portion is interposed inside the column cylinder, between the two open ends. The resin gel comprises a multiplicity of beads to which antibodies, e.g., monoclonal, polyclonal, and the like, are covalently bonded. A sample extract can be placed in the upper portion of the column and a low-pressure gas, preferably an inert gas (air), applied to the sample in the upper portion, or headspace, of the column to force the sample through the resin gel to the lower portion of the column.

In a particular use, antibodies demonstrating a high affinity for aflatoxin types, e.g., B1, B2, G1, G2, M1, and some metabolites, and other mycotoxins can be used. These particular high-affinity aflatoxin antibodies are described illustratively, however, and are not to be construed as limiting the full scope and spirit of this disclosure. As the sample percolates through the gel or is forced through the gel under an applied pressure, any or most of the aflatoxins in the sample will retain, i.e., bound, by the antibodies in the gel portion. The soluent that passes the resin gel portion can be discarded.

If the resin gel is then washed, e.g., using distilled water, to remove non-toxins that may have been retained in the resin gel and, further eluted, e.g., using high performance liquid chromatograph ("HPLC') grade methanol, the methanol solution will remove any aflatoxins retained by the antibodies and the resulting eluate can be collected and tested, e.g., in a liquid chromatograph, fluorometer, a mass spectrometer or the like, to determine the presence of toxins. For example, a developer could be added to the eluate and the eluate placed in a fluorometer.

When conditions require extensive testing for quality food processing, e.g., testing representative samples of all incoming grain at a grain elevator, high throughput is essential to avoid backing up trucks and tractor trailers, rail cars, and/or river barges delivering grain to the elevator at harvest time. Therefore, it would be desirable to provide an economical, high throughput, system for collecting and preparing samples for testing for pathogens.

SUMMARY OF THE INVENTION

The present invention provides systems and methods for isolating toxins and collecting eluate from a sample for subsequent testing to ascertain the presence of toxins in the sample.

In a first embodiment, the present invention provides a system for collecting an eluate containing toxins for subsequent testing, wherein the system comprises a sample holder, preferably an immuno-affinity column, for holding an extract of a sample containing toxins; and a self-contained fluid delivery system for delivering a plurality of liquids, e.g., reagents, and pressurized gas to the sample holder; wherein some amount of pressurized gas is provided to a headspace portion of the sample holder through the fluid delivery system continuously.

Preferably, the fluid delivery system includes a fluid control system to deliver one or more fluids in a controlled manner. Specifically, the fluid delivery system delivers low-pressure gas, preferably an inert gas (air), having a pressure between about 1 psi and about 5 psi to the column and one or more liquids, e.g., reagents, that are selected from a group comprising water, distilled water, de-ionized water, purified water, reverse osmosis water, a buffer solution, methanol, HPLC grade methanol or other reagents or eluate solutions, and the like. Preferably, the conduits for delivering the liquids are contained inside the conduit for delivering the pressurized gas.

In a preferred embodiment, each of the liquid sources comprises a dispenser for holding a liquid, e.g., a reagent; a sealing cap for sealing the opening of the dispenser; a volume selection device for precisely selecting the measured volume of liquid, e.g., reagent, to dispense; a plunger assembly for delivering the measured volume of liquid, e.g., reagent, to the sample holder; and a fluid conduit through which the measured volume of liquid, e.g., reagent, is communicated to a headspace in the sample holder.

In another aspect of the present invention, the system further comprises a stand portion, the stand portion further comprises a base portion having an upper surface for supporting and stabilizing the stand portion; a column holder portion having one or more openings for holding an equal number of sample holders, and a vertical support portion that is fixedly attached and substantially perpendicular to the upper surface of the base portion and the column support portion. When more than one openings for sample holders are provided in the column support portion, sampling and collecting an eluate from each sample holder can be controlled separately or, alternatively, the process can be controlled collectively.

In a second, embodiment, the present invention provides a method of collecting an eluate for subsequent testing using the above system. According to this embodiment, the method comprising the steps of:

providing the system;

installing a sample holder in any of one or more openings in a column holder portion of a stand portion of the system;

connecting the sample holder to the fluid delivery system using a column connection;

applying some amount of pressurized gas to the headspace portion of the sample holder continuously;

introducing a sample in the headspace portion of the sample holder;

controlling a fluid control system so that a greater amount of pressurized gas is delivered to the headspace portion to force the sample through a resin gel in the sample holder;

adding a first liquid to the headspace portion of the sample holder and forcing the first liquid through the resin gel one or more times to wash undesired components out of the column;

adding a second liquid to the headspace portion of the sample holder and forcing the second liquid through the resin gel to elute the sample; and collecting the eluate of the second liquid for subsequent testing.

Preferably, the steps of forcing the first and second liquids through the resin gel includes using a low-pressure gas, e.g., an inert gas (air), and, more preferably, the step of forcing the first and second liquids through the resin gel includes using a gas having a pressure of about 1 psi to about 5 psi.

In a preferred embodiment, the step of controlling the fluid control system includes opening a first valve lever or switch and a second valve lever or switch so that substantially all of the pressurized gas is released into the atmosphere while a small amount of pressurized gas is delivered to the headspace portion of the sample holder. Similarly, the step of controlling the fluid control system includes opening a first valve lever or switch and closing a second valve lever or switch so that substantially all of the pressurized gas is delivered to the headspace portion of the sample holder while a small amount of pressurized gas is released into the atmosphere.

BRIEF DESCRIPTION OF THE DRAWINGS

The invention will be better understood by reference to the following more detailed description and accompanying drawings where like reference numbers refer to like parts:

FIG. 3 is an illustrative embodiment of a preferred embodiment of a delivery system for the system in FIG. 2.

DETAILED DESCRIPTION OF THE INVENTION AND PREFERRED EMBODIMENTS THEREOF

In its broadest aspects, the present invention provides systems and methods for preparing samples, i.e., collecting an eluate, from a sample extract, for subsequent testing. More specifically, the present invention provides self-contained systems for preparing samples that may contain toxins, e.g., mycotoxin, aflatoxin, ochratoxin, deoxynivalenol, fumonisin, zearalenone, T2 and the like, for subsequent testing, e.g., by fluorometry, mass spectrometry, liquid chromatography, and the like.

Figure 1:
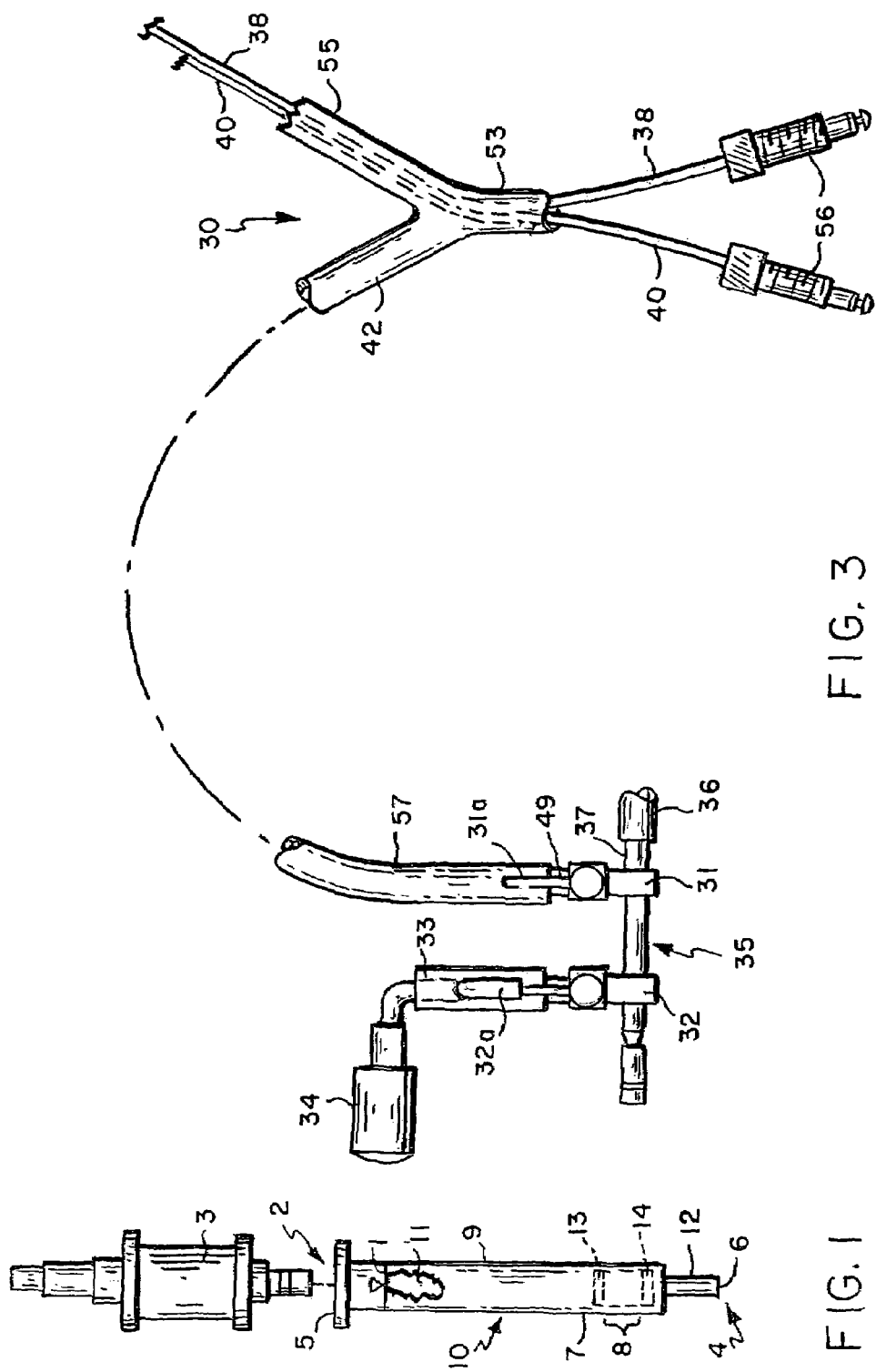
FIG. 1 is an illustrative embodiment of an immuno-affinity column and a column connection in accordance with the present invention.

Referring to FIG. 1, an illustrative embodiment of a sample holder 10, or immuno-affinity column 10, is shown. Such columns 10 are well known in the art, e.g., the Afla-Test® immuno-affinity column, and will not be described in great detail. Throughout the remainder of this disclosure, a sample holder 10 will be referred to as a column 10; however, the invention is not to be construed as being limited only thereto.

Typically, columns 10 are substantially cylindrical in shape and have openings, and more preferably circular openings, at their proximal end 2 and their distal end 4. The proximal end 2 of the column 10 is dimensioned to receive fluids, e.g., samples 1, liquids, reagents, gas, and the like, easily and also to provide a tight interference fit with a coupling device 3, e.g., a column connection 3. The proximal end 2 can include a lip, or ring, 5 that has an outer dimension that extends beyond the outer surface of the cylindrical portion 9 of the column 10 in a radial direction, to facilitate holding the column 10 in a supporting device or system (not shown). The distal end 4 is also cylindrical or can be tapered to provide a conical portion 7 having a small opening 6 through which a fluid, e.g., an eluate, can pass at the distal end 4.

Columns 10 are typically packed with a resin gel 8 that separates the column 10 into an upper portion, or headspace 11, and a lower portion 12. Preferably, the resin gel 8 comprises a plurality of beads (not shown) that contains antibodies, e.g., monoclonal, polyclonal, and the like, that are covalently bonded to the beads. More preferably, the antibodies have a high affinity for the particular toxin(s) sought in the testing. A pair of frits 13 and 14 can be disposed, respectively, on the upstream and the downstream ends of the resin gel 8. The frits 13 and 14 are, preferably, made of a porous material, e.g., a plastic, that is substantially impermeable until pressure is applied to the headspace 11, which increases the permeability of the material allowing the fluid under pressure to percolate through the beads in the resin gel 8.

In a particular use, antibodies demonstrating high affinity for mycotoxins, and, more specifically, aflatoxin types B1, B2, G1, G2, and M1, and some metabolites, can be used. As the sample 1 is forced through the resin gel 8 under an applied pressure, any or most of the aflatoxins in the sample 1 will be bound to the antibodies in the resin gel 8.

If the resin gel 8 is then eluted with a solvent, e.g., using high performance liquid chromatograph ("HPLC") grade methanol, acetonitrile, and the like, the methanol solution will remove any aflatoxins bound to the antibodies and the resulting eluate can be collected and tested, e.g., by liquid chromatography, fluorometry, mass spectrometry, and the like, to determine the presence of toxins in the sample. For example, a developer could be added to the eluate and the eluate placed in a fluorometer.

Figure 2:
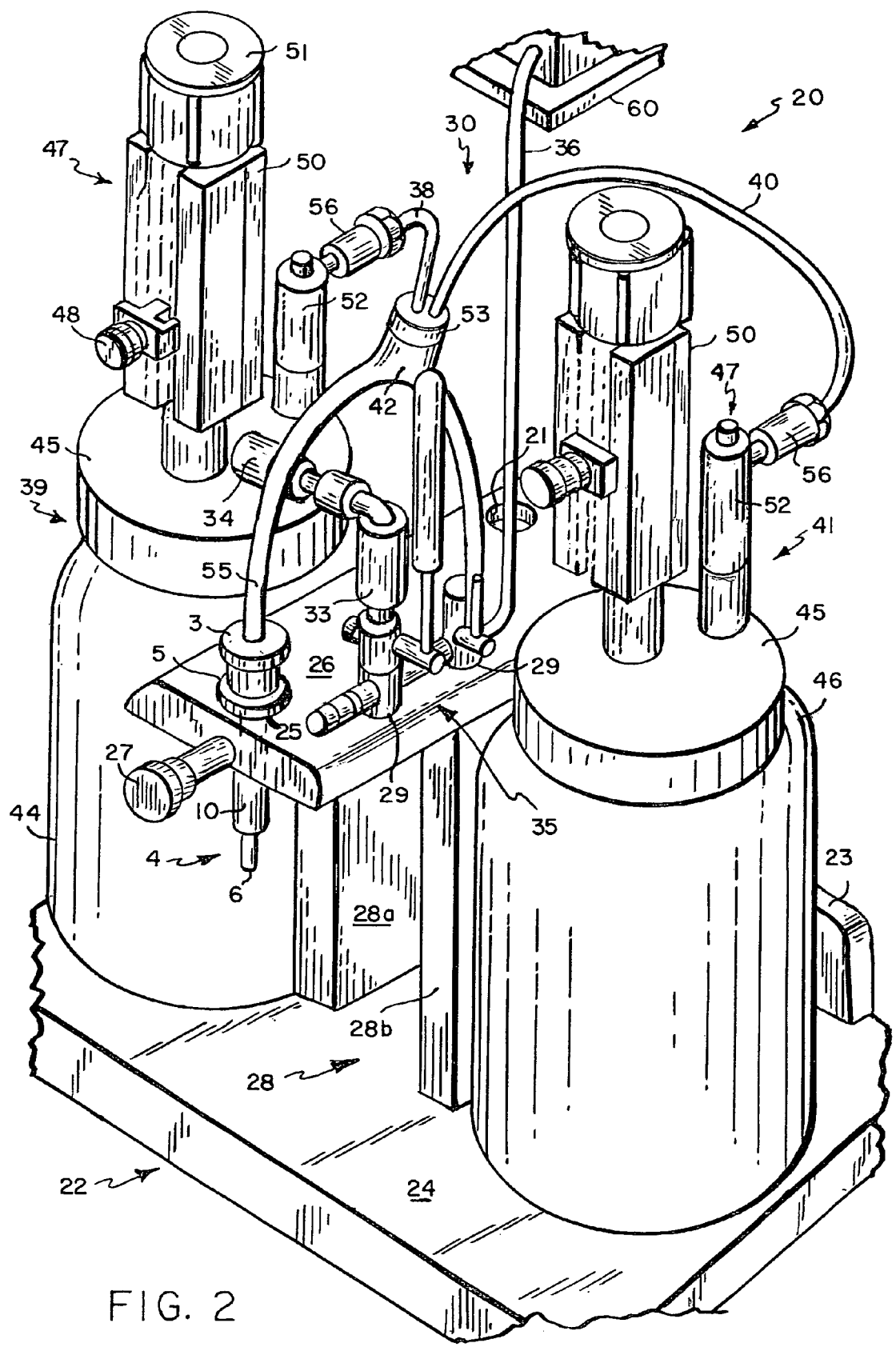
FIG. 2 is an illustrative embodiment of a system for isolating toxins and collecting eluate for testing for toxins in accordance with the present invention.

Having described a column 10 for holding a sample 1, we will now describe a system 20 for collecting a sample 1 containing a toxin for subsequent testing for the same. In a preferred embodiment, the system 20 includes a stand portion 22 and a delivery system 30. Referring to FIG. 2, the stand portion 22 includes a base portion 24 to provide stability and support to the entire system 20; a column holder portion 26 having one or more openings 25 for receiving and supporting an equal number of columns 10; a vertical support portion 28 that is fixedly attached to base portion 24 at one end and to the column holder portion 26 at the other end; and a back portion 23.

In a preferred embodiment, the base portion 24 is structured and arranged to support itself, the delivery system 30, a plurality of liquid, e.g., reagent containers 44 and 46, and the one or more sampling columns 10 and, particularly, to provide a stable working platform. Although FIG. 2 shows a system 20 having a single sampling column 10 for which dimension of 6 inches by 9 inches work satisfactorily, the invention is not to construed as being limited to a single opening 25. Indeed, the system 20 of the present invention can include a plurality of openings 25 for receiving an equal number of sampling columns 10 without violating the scope and spirit of the disclosure.

The base portion 24 can be made of any material, e.g., acrylic, metal, metal alloy, plastic, wood, glass, and the like. However, as a matter of practicality, the material selected should be sturdy, inexpensive to manufacture, and easily maintained, e.g., cleaned or autoclaved. When used in food quality processing, it also may be desirable that the material be compatible with the food-processing environment. Moreover, the material selected should not react with any of the reagents used during the sampling process. To provide greater resistance to sliding along a working surface or platform, a plurality of feet (not shown), e.g., rubber, neoprene, and the like, can be fixedly attached, e.g., adhesively attached, to the underside of the base portion 24.

Preferably, the column holder portion 26 is manufactured of the same material as the base portion 24. However, different materials can be used without violating the scope and spirit of this disclosure. Here again, as a matter of practicality, the material selected should be sturdy, inexpensive to manufacture, and easily maintained, e.g., cleaned or autoclaved. The column holder portion 26 includes one or more openings 25 for receiving and supporting an equal number of testing columns 10. Optionally, in order to restrain more securely the one or more sampling columns 10 in the openings 25, a locking device 27, e.g., a thumbscrew 27, can be included. The design and function of thumbscrews 27 are well known to the art and will not be described further. Those of ordinary skill in the art will appreciate that there are a myriad of novel ways of securing a column 10 in an opening 25, which are all within the scope and spirit of this disclosure.

In a preferred embodiment, the column holder portion 26 also includes one or more insert, or recess holes 29 for receiving and the supporting valve portion 35 of the delivery system 30. Optionally, one or more openings 21 for conduits can be included to rout the flexible tubing used for the many fluid conduits underneath the column holder portion 26 and to provide a more orderly appearance.

The vertical support portion 28 is structured and arranged to elevate and support the column holder portion 26. Preferably, the vertical support portion 28 is manufactured of the same material as the base portion 24 and the column holder portion 26. However, different materials can be used without violating the scope and spirit of this disclosure. Once again, as a matter of practicality, the material selected should be sturdy, inexpensive to manufacture, and easily maintained, e.g., cleaned or autoclaved. Selecting like materials facilitates fixedly attaching, e.g., adhesively attaching, the vertical support portion 28 to the column holder portion 26 and the base portion 24.

Although FIG. 2 shows a vertical support portion 28 comprising a left support 28a and a right support 28b, the invention is not to be limited thereto. Indeed, the vertical support portion 28 should be structured and arranged to best support and stabilize the column holder portion 26. Accordingly, the vertical support portion 26 can be made of one or more pieces. The vertical support portion 28 should be further structured and arranged to elevate the column holder portion 26 a sufficient height to provide enough working space to collect fluids and/or eluate from the opening 6 at the distal end 4 of the column 10 without difficulty.

The back portion 23 is provided as a splashguard and, further, to keep any liquid, e.g., reagent, containers 44 or 46 from sliding off the back of the base portion 24. Preferably, the back portion 23 is manufactured of the same material as the base portion 24. However, different materials can be used without violating the scope and spirit of this disclosure. As a matter of practicality, though, the material selected should be sturdy, inexpensive to manufacture, and easily maintained, e.g., cleaned or autoclaved. Selecting like materials facilitates fixedly attaching, e.g., adhesively attaching, the back portion 23 to the base portion 24.

Optionally, for greater stability of the liquid, e.g., reagent, containers 44 or 46, the vertical support portion 26 can include a securing device for releasably securing one or more of the liquid, e.g., reagent, containers 44 or 46 to the vertical support portion 26. Preferably, the securing device is a portion of a Velcro® strip that is fixedly, e.g., adhesively, attached to the vertical support portion 28 and removably or fixedly attached to the liquid, e.g., reagent, containers 44 or 46. Alternatively, just a single strap can be fixedly attached to the vertical support portion 26 to wrap around the liquid, e.g., reagent, container 44 or 46.

Having described the stand portion 22 of the system 20, we will now describe the fluid delivery system 30. Referring to FIGS. 2 and 3, an illustrative example of a preferred embodiment of the fluid delivery system 30 is shown. Preferably, the embodied delivery system 30 is self-contained and can deliver one or more fluids, e.g., gas, liquid, reagents, and the like to the headspace 11 of the column 10 without having to remove the column connection 3 once the column connection 3 is placed in a tight interference fit at the proximal end 2 of the column 10.

Advantageously, the self-contained nature of the present invention makes sampling faster because it is not necessary to remove the column connection 3 before and after the washing step and before and after the elution step. More advantageously, the delivery portion 30 of the system 20 minimizes cleaning requirements and, furthermore, the current delivery portion 30 of the system 20 minimizes the amount of some of the liquids, e.g., methanol, water, used in the process.

The delivery portion 30 of the system 20 comprises a first liquid conduit 38, a second liquid conduit 40, a T- or Y-shaped conduit connection 42, a column connection 3, a gas control system 35, and a gas conduit 36. Preferably, the first liquid conduit 38 is in fluid communication with a first liquid dispenser 39 for dispensing, e.g., reagents such as water, distilled water, de-ionized water, purified water, reverse osmosis water, buffer solution, methanol, HPLC-grade methanol, other elution solutions, and the like, into the headspace 11 of the column 10 and the second liquid conduit 40 is in fluid communication with a second liquid dispenser 41 for dispensing, e.g., reagents such as water, distilled water, de-ionized water, purified water, reverse osmosis water, buffer solution, methanol, HPLC-grade methanol, other elution solutions, and the like, into the headspace 11 of the column 10. Although, only two liquid dispensers 39 and 41 and two liquid conduits 38 and 40 are shown in FIG. 2, this is done for illustrative purposes only and the invention is not to be construed as being so limited. Indeed, there can be more than two liquid dispensers 39 and 41 and more than two liquid conduits 38 and 40 without violating the scope and spirit of this disclosure. Moreover, there can be more ways of dispensing liquids. The one chosen by the inventors is simple yet robust.

For the remainder of this disclosure the liquid dispensers and liquid conduits will be referred to as reagent dispensers and reagent conduits; however, the invention is not to be construed as being limited solely to reagents and/or liquid reagents. Preferably, the first and second reagent dispensers 39 and 41 are structured and arranged for dispensing reagents such as water, distilled water, de-ionized water, purified water, reverse osmosis water, buffer solution, methanol, HPLC-grade methanol, other elution solutions, and the like. In a preferred embodiment, the dispensers 39 and 41 each include a reagent container 44 and 46 with a sealing cap 45 and a precision fluid dispensing unit 47, e.g., a MILLIMATIC dispenser manufactured by TriContinent of Grass Valley, Calif. The sealing caps 45 are removably securable about the opening of the reagent containers 44 and 46. The precision dispensing unit 47, which is integral with or separate from the sealing cap 45, should have a dispensing range between about 0.25 and about 14.9 mL with a factory calibrated accuracy of between about ±0.05 to 0.1 mL and a precision of about ±1 percent.

Plunger-type fluid dispensing units 47, such as the MIILIMATIC, can include a volume selector 48 that can be set with a high degree of accuracy to deliver a precise fluid volume into the headspace 11 of the column 10. Typically, fluid volumes between about 0.5 and 3.0 mL will satisfactorily fill the headspace 11 volume of most columns 10. However, larger columns 10 having greater headspace 11 volumes, e.g., about 14.9 mL, are also within the teachings of this disclosure.

Once the plunger assembly 50 is activated, e.g., typically, by applying an upward then a downward pressure to the top 51 of the plunger assembly 50, the precise fluid volume is delivered to the headspace 11 of the column 10 through, successively, an outlet 52 and a reagent conduit 38 or 40. Preferably, the first and second reagent conduits 38 and 40 are made of flexible tubing each having a diameter much smaller that the diameter of the main conduit 55 and having a length that extends all the way through the main conduit 55 and the column connection 3. This way, the precise fluid volume is delivered directly into the headspace 11 of the column 10 with little or no volume loss due to adsorption, surface tension, and the like on the inside surface of the main conduit 55 or the column connection 3 and to eliminate or minimize reagent interaction with the surfaces of the conduit 55 and the column connection 3.

Preferably, the reagent conduits 38 or 40 are removably secured to the outlet 52 using a friction fit. Alternatively, when a commercially available plunger-type fluid dispensing units 47, such as the MIILIMATIC, is used, it may be necessary to adapt a special fitting 56 to the outlet 52 if the inner diameter of the reagent conduits 38 or 40 is not compatible with the outer dimension of the outlet 52. Such adaptation is well within the knowledge of those skilled in the pertinent art and will not be discussed in greater detail.

Having described an embodiment of that portion of the delivery system 30 that communicates reagents to the headspace 11 of the column 10, we will now discuss the portion of the delivery system 30 that communicates pressurized gas, e.g., compressed air, to the headspace 11 of the column 10. During an operational stage, which will be defined in greater detail in our discussion of a second embodiment, the gas control system 35 communications pressurized gas, e.g., compressed air and the like, from a gas pump 60, e.g., 110 Volt gas (air) pump 60 capable of producing between about 1 and about 5 pounds per square inch ("psi") of pressure, such as those produced by Bianca Products, Inc. of Temecula, Calif. Preferably, the gas (air) is delivered into the headspace 11 of the column 10, successively, via a gas conduit 36, a first valve 31, a second fitting 49, a lower conduit 57, the T- or Y-shaped conduit connection 42, the main conduit 55, and the column connection 3.

Necessarily, the base portion 53 of the T- or Y-shaped conduit connection 42 through which the reagent conduits 38 and 40 enter the main conduit 55 is structured and arranged to minimize loss of gas pressure, e.g., airtight, to prevent pressurized gas from escaping therethrough. Those of ordinary skill in the art are familiar with a myriad of ways to make the base portion 53 of the T- or Y-shaped conduit connection 42 airtight without otherwise affecting, e.g., crimping or otherwise obstructing the inner passageway of, the reagent conduits 38 and 40.

During the non-operational stage, which also will be defined in greater detail in our discussion of a second embodiment, the gas control system 35 communicates the majority of the pressurized gas, e.g., compressed air and the like, from the gas (air) pump 60 into the atmosphere. However, even during a non-operational stage, a small fraction of the pressurized gas is still communicated into the headspace 11 of the column 10. The inventors have discovered that by allowing the gas pump 60 to run continuously and to provide positive pressure continuously during the operational and the non-operational stages of the sampling process, the sampling process will take about one-third or less time to complete than is the case when the gas pump 60 is ON only during the operational stage and completely OFF during the non-operational stage.

The gas control system 35 includes two, controllable valves 31 and 32 that are structured and arranged in series. The gas conduit 36, e.g., flexible tubing, is removably attached by a friction fit to a first fitting 37 that is located adjacent to the first valve lever, or switch, 31$a$. When the first valve lever, or switch, 31$a$ is oriented in an UP direction, the first valve 31 is open. As a result, the pressurized gas entering the first fitting 37 passes through the first valve 31 towards the second valve 32 and/or is redirected through a second fitting 49 to which the lower conduit 57 is removably attached. How much or how little of the pressurized gas enters the latter is determined by the position of the second valve lever, or switch, 32$a$.

When the second valve lever, or switch, 32$a$ also is oriented in an UP direction, the second valve 32 is also open. As a result, most, but not all, of the pressurized gas entering the first fitting 37 passes directly through first valve 31 into the second valve 32 and through a bleeder valve 33. An air stone 34 can be removably attached to the bleeder valve 33, to minimize the noise of the pressurized gas escaping into the atmosphere. Some small fraction of the compressed gas, however, still passes from the first valve 31 through the second fitting 49 and is communicated into the headspace 11 of the column 10. Accordingly, when both valve levers, or switches, 31$a$ and 32$a$ are oriented the UP direction, substantially all of the pressurized gas is released into the atmosphere, a small fraction of pressurized gas, however, is still communicated into the headspace 11 of the column 10.

When the first valve lever, or switch, 31$a$ is oriented in an UP direction but the second valve lever, or switch, 32$a$ is oriented in an orthogonal direction or in a direction between orthogonal and straight UP, the second valve 32 is fully closed (orthogonal) or partially closed (in between). As a result, when the second valve lever, or switch, 32$a$ is in an orthogonal or an "in-between" orientation, the pressurized gas entering the first fitting 37 passes through the first valve 31 into the second fitting 49 and is communicated into the headspace 11 of the column 10. To control the rate at which the sample 1 is forced through the resin gel 8, the second valve switch 32$a$ can be adjusted towards the UP direction to slow down the rate of the process or towards the orthogonal direction to speed up the rate of the process.

Figure 4:
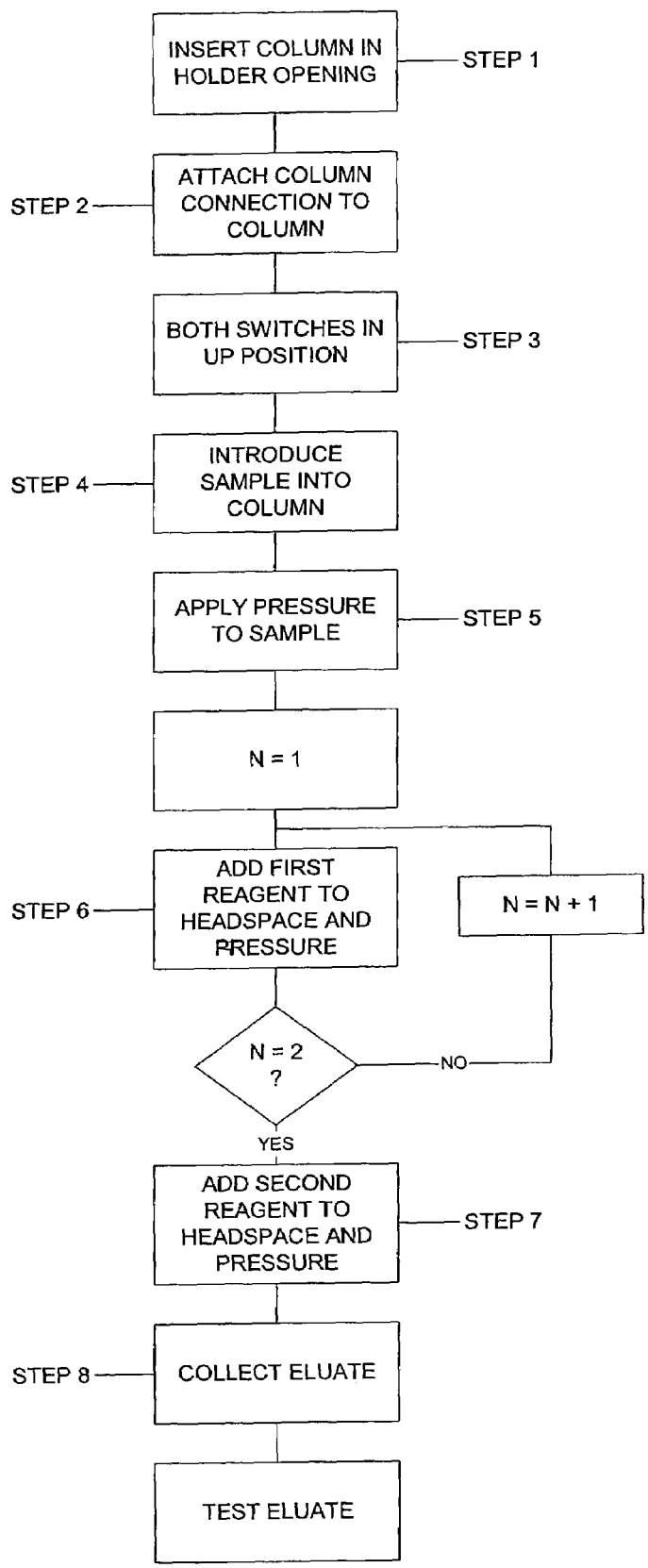
FIG. 4 is a flow chart of a method for collecting an eluate for testing for toxins using the system in FIG. 2.

Having described systems for collecting eluate from a sample in a column, we will now describe a second embodiment of the present invention that provides methods of collecting eluate from samples using these systems. A flow chart of process steps is provided in FIG. 4.

In a first step, users insert a new sampling column, e.g., an AflaTest® type column, into any of the openings in the column holder portion of the stand portion of the system (STEP 1). Typically, AflaTest® type column come with protective caps covering the opening at their proximal and distals ends. If this is the case, the protective caps should be removed prior to insertion into any of the openings of the column holder portion. Optionally, the column can be further restrained in the opening by tightening a thumbscrew or other locking device provided for that purpose to a desired pressure. Once the column has been inserted in the opening, the column connection can be inserted into the opening at the proximal end of the column until a tight interference fit is achieved (STEP 2). Those skilled in the art can appreciate that the sequence of STEPS 1 and 2 are interchangeable as it matters not whether the column connection is fit into the opening of the column before or after the column is inserted in any of the openings in the column holder portion.

The first and second reagent dispensers (and any other reagent dispensers if there are more than two) should be filled with desired reagents and the reagent dispensers should be capped with a sealing cap having a precision fluid dispensing unit and, further, structured and arranged to deliver a discrete volume of reagent to the headspace of the column. For example, the reagent dispensers can be filled with any of the following liquids: water, distilled water, de-ionized water, purified water, reverse osmosis water, buffer solution, methanol, HPLC-grade methanol, other elution solutions, and the like. For illustrative purposes, for the remainder of this disclosure, the first reagent will be distilled water and the second reagent will be HPLC-grade methanol. Furthermore, for illustrative purposes only, the precision fluid dispensing unit can be set beforehand to dispense 1 mL of the reagent (for use with a column having a headspace volume of about 1 mL). Typically, if the fluid dispensing unit is a plunger-type unit, it may be necessary to prime the unit so that the desired volume of the reagent is in the dispensing unit with no air bubbles.

Before sampling, the user must ensure the quality of the reagents being used. To properly accomplish this step, the reagents should be processed in the testing device e.g., by fluorometry, that will be used to test the eluate to be collected. Accordingly, it is necessary to calibrate the fluorometer using the appropriate calibration standards. Those skilled in the art are well familiar with ways to calibrate the fluorometer. Then, once the fluorometer is calibrated, samples of the first reagent, i.e., distilled water, and the second reagent, i.e., the HPLC-grade methanol, can be tested in the same. As an illustrative example, volumes of the HPLC-grade methanol and distilled water, e.g., 2 mL of each, can be dispensed from the appropriate reagent dispenser into, e.g., separate glass cuvettes. The glass cuvettes containing the reagents are then placed in the fluorometer. The results should be zero; however, in the event that one or both is not, the process should be repeated. If the fluorometer again does not register zero, the failing reagent(s) should be replaced.

In the next step, the first and second valve levers, or switches, should each be oriented in the UP direction so that the first and second valves are open (STEP 3). As provided above, this corresponds to the non-operational stage of the process. With both valve levers, or switches, in the UP position, flow of the gas (air) from the pump can be slowly raised to a desired pressure. Preferably, the gas (air) pump can provided a controllable pressure of between about 1 and about 5 psi of positive pressure. In the non-operational stage, substantially all, but not all, of the gas (air) escapes into the atmosphere through the bleeder valve of the second valve. An air stone affixed to the end of the bleeder valve can muffle the noise of the escaping gas under pressure.

Typically, sampling columns are shipped containing a buffer in the headspace. The buffer can be poured out, or more preferably, with the column connected to the fluid delivery system, the second valve lever, or switch, can be rotated from the UP direction, forcing the pressurized gas (air) into the headspace of the column. Preferably, the pressurized gas (air) is controlled by rotating the second valve lever, or switch, sufficiently to produce a liquid flow out of the column of only about one (1) drop per second. The headspace should not be allowed to run dry unless the sampling process is completed.

The sample extract can then be introduced into the sampling column (STEP 4). For example, users can place a discrete volume of a liquid sample, e.g., about 1 to 3 mL, into the headspace of the column. The sample can be introduced into the headspace while the column is secured in any of the openings of the column holder portion or, preferably, the column can be removed from the column holder portion; any buffer remaining in the headspace can be shaken out; the discrete volume of liquid sample can be introduced into the headspace; the column re-inserted and re-secured in one of the openings in the column holder portion; and the column connection re-attached in the opening at the proximal end of the column, providing a tight interference fit.

With the sampling column containing the sample now attached to the sampling apparatus via the column connection, the second valve lever, or switch, can be rotated from the UP direction to force more low-pressure gas (air) into the headspace, forcing the sample through the resin gel (STEP 5). Preferably, the second valve lever, or switch, is again adjusted to provide a flow rate of about one (1) drop per second. As the sample is forced through the resin gel, toxins in the sample are bound to the antibodies that are covalently bonded to the beads. Once the entire volume of sample has passed through the resin gel, the pressurized gas can still be applied to the headspace so that some of the gas also passes through the resin.

Without removing the column connection, a discrete amount, e.g., 1 mL, of the first reagent, i.e., distilled water, can then be added to the headspace of the column and passed through the resin gel under the force of the pressurized gas (STEP 6). This step is called the washing step as undesired particles that may also have bound to the antibodies or otherwise retained in or by the beads are washed away from the beads. If a plunger-type dispensing unit is used, the distilled water can be added by pulling up then pressing down on the plunger. Here again, the second valve lever, or switch, is adjusted to provide a flow rate of about one (1) drop per second. Once the entire volume of distilled water has passed through the resin gel, the pressurized gas is still applied to the headspace so that some of the gas also passes through the resin gel. This process of adding distilled water to the headspace can be repeated one or more times.

The second valve lever, or switch, can then be rotated to or re-oriented in the UP position, i.e., non-operational position, so that substantially all, but not all, of the pressurized gas (air) escapes into the atmosphere through the bleeder valve of the second valve. With the second valve lever, or switch, re-oriented in the UP direction, a discrete amount, e.g., 1 mL, of the second reagent, i.e., HPLC-grade methanol, can then be added to the headspace of the column and passed through the resin gel under the force of the pressurized gas (STEP 7). This step is called the elution step as toxins bound to the antibodies are eluted away by the liquid reagent. If a plunger-type dispensing unit is used, the HPLC-grade methanol can be added by pulling up then pressing down on the plunger.

Once HPLC-grade methanol has been introduced into the headspace of the column, the second valve lever, or switch, is adjusted to provide a flow rate of about one (1) drop per second. The HPLC-grade methanol removes any toxins that were bound to the antibodies. The eluate, which is that liquid that exits the resin gel, should be collected (STEP 8), e.g., in a glass cuvette, for subsequent testing, e.g., by fluorometry, mass spectrometry, liquid chromatography, and the like. Typically, this involves adding a developer to the eluate and placing the eluate in a fluorometer to measure the presence of any toxins in parts per billion. Although the invention has been described for testing eluates by fluorometry, the invention is not to be construed as being so limited. For example, eluates can also be tested by liquid chromatography, e.g., thin liquid chromatography ("TLC"), mass spectrometer/liquid chromatography ("MS/LC"), and the like.

Once the entire volume of HPLC-grade methanol has passed through the resin, the elution and sampling process is completed and the gas (air) compressor can be turned off and the sampling column removed and discarded, if necessary.

Although preferred embodiments of the invention have been described using specific terms, such descriptions are for illustrative purposes only, and it is to be understood that changes and variations may be made without departing from the spirit or scope of the following claims.

For example, although the invention has been described to include manually rotating a lever to control the flow of pressurized gas to the headspace of the sampling column, those of ordinary skill in the art will appreciate that such a system could be further automated to include switches instead of levers to control gas flow.

Furthermore, although the invention has been described for single opening embodiment, the system can include multiple openings. When more than one column is being processed at any given time, the sampling process in each column can be controlled by a single fluid delivery system or each column can be controlled individually by a fluid delivery system dedicated to that particular column.

What is claimed is:

1. A system for collecting an eluate containing an analyte for subsequent testing, the system comprising:
    (a) a sample holder for holding an extract of a sample containing a toxin, the sample holder defining a headspace portion; and
    (b) a fluid delivery system in fluid communication with the sample holder for delivering a plurality of liquids and pressurized gas to the sample holder;
    wherein the fluid delivery system includes:
        (i) a pressurized gas source for providing the pressurized gas;
        (ii) one or more fluid conduits for dispensing liquids to the sample holder;
        (iii) a three-ended conduit connection for routing liquids dispensed by the one or more fluid conduits; a first end of the three-ended conduit connection being sealingly engaged around the one or more fluid conduits such that the one or more fluid conduits pass through a second end of the three-ended conduit connection, which is connected to the sample holder;
        (iv) a gas conduit connected to the pressurized gas source for dispensing the pressurized gas provided;
        (v) a first valve connected between the gas conduit and a third end of the three-ended conduit connection;
        (vi) a second valve connected in series with the first valve; and
        (vii) a bleeder valve connected to the second valve, wherein
        when the first valve is open, pressurized gas may pass through the first valve toward the second valve and the third end,
        when the second valve is open, a major portion of the pressurized gas passing through the first valve enters the second valve and, thereby, passes to atmosphere through the bleeder valve while a minor portion of the pressurized gas passing through the first valve enters the third end and, thereby, passes to the headspace portion, and
        when the second valve is closed, the pressurized gas passing through the first valve enters the third end and, thereby, fully passes to the headspace portion.

2. The system as recited in claim 1, wherein the analyte is a toxin.

3. The system as recited in claim 2, wherein the toxin is a mycotoxin.

4. The system as recited in claim 3, wherein the mycotoxin is selected from a groups comprising aflatoxin, ochratoxin, deoxynivalenol, fumonisin, zearalenone, and T2.

5. The system as recited in claim 1, wherein the sample holder is an immuno-affinity column.

6. The system as recited in claim 5, wherein the immuno-affinity column is substantially cylindrical in shape having openings at a proximal and a distal end of the column and wherein a resin gel is disposed inside of the column between its proximal and distal ends to define a headspace portion and a lower portion.

7. The system as recited in claim 1, wherein the liquids of the plurality of liquids are liquid reagents.

8. The system as recited in claim 7, wherein the liquid reagents are selected from a group comprising water, distilled water, de-ionized water, purified water, reverse osmosis water, buffer solution, methanol, HPLC grade methanol, and elution solutions.

9. The system as recited in claim 1, wherein the fluid delivery system includes a fluid control system to deliver one or more fluids in a controlled manner.

10. The system as recited in claim 9, wherein the fluid control system includes a plurality of valves, each valve having a valve lever that opens and closes said valve to control the amount of fluid that is delivered to a headspace contained in the sample holder.

11. The system as recited in claim 9, wherein the fluids to be delivered in a controlled manner are selected from a group comprising pressurized gas, compressed air, water, distilled water, de-ionized water, purified water, reverse osmosis water, buffer solutions, methanol, a HPLC grade methanol, and elution solutions.

12. The system as recited in claim 1, wherein the fluid delivery system is in communication with a source of liquid.

13. The system as recited in claim 12, wherein the source includes:
    a dispenser for holding the liquid, having an opening;
    a sealing cap for sealing the opening of the dispenser, wherein the sealing cap includes a delivery opening; and
    a plunger assembly for delivering a measured volume of liquid to the sample holder, wherein the plunger assembly is in fluid communication with and removably attached to the delivery opening of the sealing cap, wherein the plunger assembly includes:

a volume selection device for precisely selecting the measured volume of liquid to dispense for delivery to the sample holder; and a fluid conduit through which the measured volume of liquid is communicated to a headspace in the sample holder.

14. The system as recited in claim 1, wherein pressurized gas is delivered to the sample holder in a conduit that is releasably attached at a distal end of a column to a column connection.

15. The system as recited in claim 14, wherein the column connection for coupling the fluid delivery system to the sample holder further comprises at least one of an air-tight seal and a water-tight seal.

16. The system as recited in claim 1, wherein the fluid delivery system includes a column connection for connecting the one or more fluid conduits of the fluid delivery system to the sample holder.

17. The system as recited in claim 1, wherein the fluid delivery system delivers low-pressure gas having a pressure between about 1 psi and about 5 psi.

18. The system as recited in claim 1, said bleed off valve has an air stone.

19. The system as recited in claim 1, wherein the system further comprises a stand portion attached to the fluid delivery system for providing support to the system, the stand portion further comprising:

a base portion, having an upper surface, for supporting and stabilizing the stand portion;

a holder portion having one or more openings for holding an equal number of sample holders, wherein the holder portion is substantially parallel to the upper surface of the base portion, and a vertical support portion that is fixedly attached and substantially perpendicular to the upper surface of the base portion and the holder portion.

20. The system as recited in claim 19, wherein the vertical support portion includes one or more dispensers and a securing device for releasably securing the one or more dispensers to the holder portion.

21. The system as recited in claim 19, wherein the stand portion further comprises a back portion that is fixedly attached to and in an orthogonal relationship with the base portion to provide a splashguard and to prevent any objects on the base portion from sliding off.

22. The system as recited in claim 14, wherein the fluid delivery system is further configured to deliver the plurality of liquids to the sample holder without having to remove the column connection once the column connection is placed in a tight interference fit at a proximal end of the column.

23. The system as recited in claim 1, wherein the one or more fluid conduits comprises: a first reagent conduit and a second reagent conduit, each of the first and second reagent conduits having 1) a diameter smaller than a diameter of the first end of the three-ended conduit, and 2) a length extending through the first end of the three-ended conduit.

24. The system as recited in claim 1, wherein a portion of the sample holder is packed with a resin gel for defining the sample holder into a headspace and a lower portion.

25. The system as recited in claim 24, further comprising a pair of frits disposed on either side of the resin gel for increasing a permeability of fluid passing through the resin gel within the sample holder, when pressure is applied to the headspace.

26. A system as recited in claim 1, wherein when the second valve is partially closed, an amount of the pressurized gas passing through the first valve and entering the third end varies in relation to an amount of closure of the second valve.

* * * * *